United States Patent [19]

Fine

[11] Patent Number: 4,515,771

[45] Date of Patent: May 7, 1985

[54] COMPOSITION AND METHOD FOR THE PREVENTATIVE TREATMENT OF DENTAL DISEASE AND APPARATUS FOR DISPENSING SAID COMPOSITION

[76] Inventor: Daniel H. Fine, 41 Brook Ter., Leonia, N.J. 07605

[21] Appl. No.: 483,660

[22] Filed: Apr. 11, 1983

[51] Int. Cl.³ .............................................. A61K 7/18
[52] U.S. Cl. ........................................ 424/52; 424/54
[58] Field of Search .................. 424/49, 52, 54, 255, 424/263, 280

[56] References Cited

U.S. PATENT DOCUMENTS

| | | | |
|---|---|---|---|
| 173,607 | 2/1876 | Fehr | 424/49 |
| 2,449,184 | 9/1948 | Strean | 424/52 |
| 2,470,906 | 5/1949 | Taylor | 424/49 |
| 2,837,463 | 6/1958 | Fosdick et al. | 424/49 |
| 3,228,844 | 1/1966 | Strean | 424/49 |
| 3,282,778 | 11/1966 | Gobel | 424/52 |
| 3,886,265 | 5/1975 | Evers et al. | 424/49 |
| 3,925,543 | 12/1975 | Donohue | 424/52 |
| 3,992,519 | 11/1976 | Hofmann et al. | 424/49 X |
| 4,229,430 | 10/1980 | Fahim et al. | 424/49 |
| 4,363,794 | 12/1982 | Ochiai et al. | 424/49 X |

*Primary Examiner*—George F. Lesmes
*Assistant Examiner*—Nancy A. B. Swisher
*Attorney, Agent, or Firm*—Bauer & Amer; Bauer & Amer

[57] ABSTRACT

An oral composition for the preventative treatment of dental disease is provided. The composition includes an active ingredient selected from the group consisting of ascorbic acid, pyridoxine hydrochloride, and an anti-inflammatory agent admixed in a vehicle including a gelling agent. Sodium fluoride may also be included. Method and apparatus for dispensing this composition are further provided.

14 Claims, 2 Drawing Figures

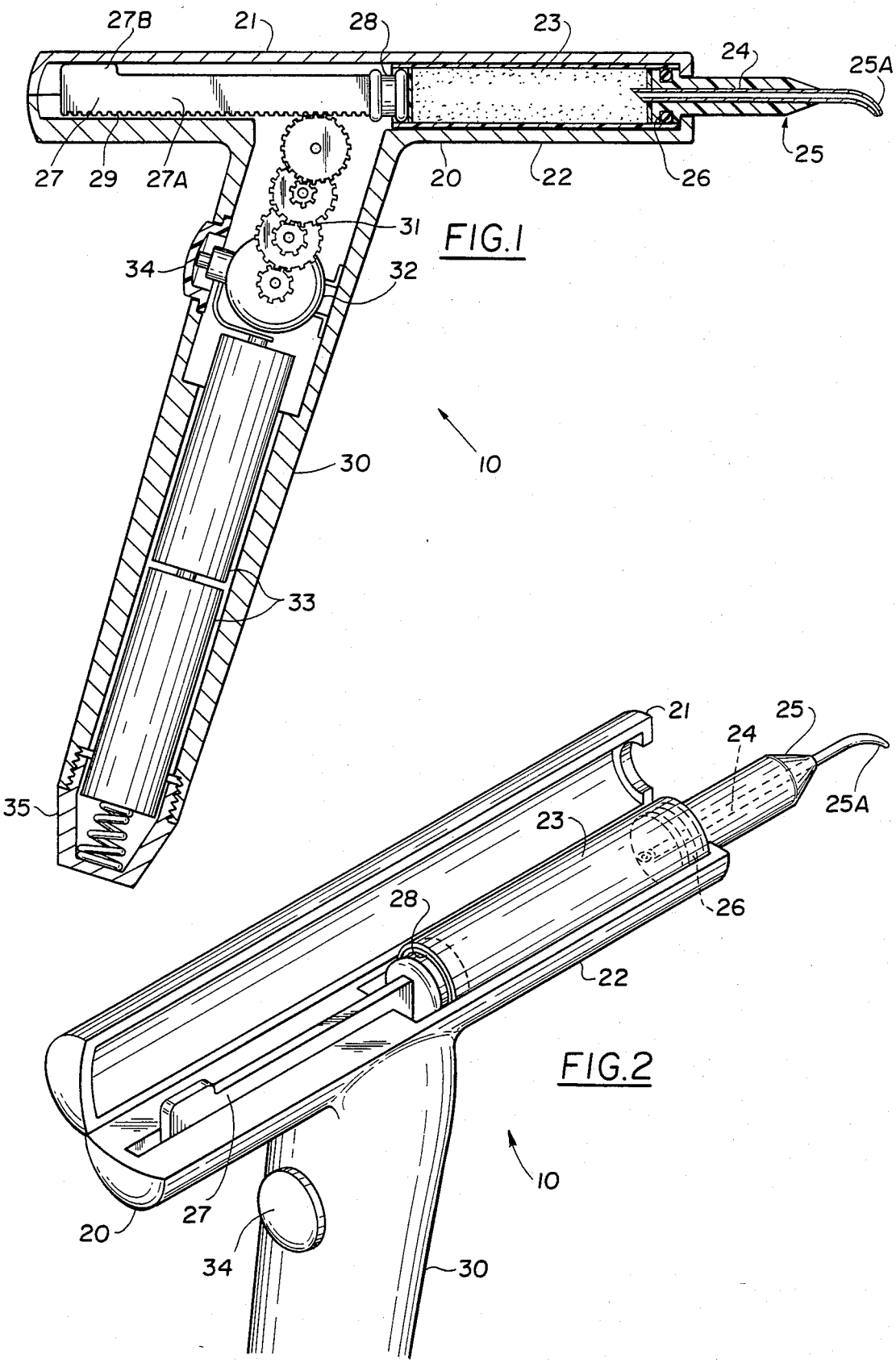

COMPOSITION AND METHOD FOR THE PREVENTATIVE TREATMENT OF DENTAL DISEASE AND APPARATUS FOR DISPENSING SAID COMPOSITION

BACKGROUND OF THE INVENTION

The present invention relates generally to composition and method for the preventative treatment of the initiation and progression of bacterially-induced, dental disease including periodontal disease and apparatus for dispensing said composition. The composition includes an active ingredient selected from the group consisting of ascorbic acid and pyrodoxine hydrochloride admitted in a vehicle which includes a gelling agent. The method involves delivery of the composition, in gel form, to a point between the patient's gum and teeth where it may effectively come in contact with the types of bacteria which typically becomes entrapped and cause disease beneath the gum line. Apparatus is provided for dispensing the composition directly to the disease site beneath the gum line.

A tooth, which is composed of a crown and root, is supported or otherwise anchored in the mouth by fibers which connect the root to the jawbone. The crown, which is enamel and visible, provides the chewing or masticating surface while the root, which is embedded in the jawbone, is covered by gum tissue which surrounds the neck of the crown. Periodontal disease, i.e., pyorrhea, is primarily caused by oxygen-sensitive, nutritionally fastidious, subgingival microorganisms, i.e., bacteria which accumulate on the crowns of the teeth beneath the gum line and between the crown and the gum. Bacteria which accumulate beneath the gum line are generally inaccessible to ordinary prophylactic devices such as tooth brushes, floss and mouth wash. Removal of these bacteria is normally accomplished by physical disruption of the bacterial mass by a dentist or hygienist during regularly scheduled scaling and cleaning sessions.

As periodontal disease progresses, the separation between the crown and the gum becomes wider and deeper and bacterial elimination or cleaning with ordinary prophylactic devices becomes even more problematic. Since periodontal disease is usually chronic and progressive in nature, it is advantageous to control or prevent its development.

It is widely acknowledged that periodontal disease is the principal cause of tooth loss. Cost of dental care has escalated dramatically in recent years and is expected to increase even more in the future due to an expanded patient pool resulting from an increase in life expectancy and an increased awareness of the need for treatment.

Although a number of gel products have recently been introduced on the market to clean teeth and gums and to kill bacteria on the surface thereof, such products have generally proven ineffective in penetrating to the interstices which exist between the gum and teeth in order to attack the bacteria where they exist. This inability is, in part, due to the manner in which such products are applied, i.e., to the gum or tooth surface rather than to the spaces between the gum and teeth. Additionally, their inability to effectively prevent periodontal disease is caused by the lack of potency of the compositions themselves.

Many of the prior art compositions for the preventive treatment of periodontal disease include a fluoride in one form or the other. For example, U.S. Pat. No. 4,267,167, which issued on May 12, 1981 to Stewart Weitzman et al., teaches a thixotropic acid-related phosphate fluoride composition; U.S. Pat. No. 4,272,513, which issued on June 9, 1981 to Abdul Gaffar, teaches an oral composition including a fluorine-containing anticaries agent; U.S. Pat. No. 3,666,855, which issued on May 30, 1972 to Joseph C. Muhler, teaches an oral composition including ammonium salts of condensation products of ammonia and phosphorous pentoxide; and U.S. Pat. No. 3,337,412, which issued on Aug. 22, 1967 to Charles H. Elbreder, teaches a therapeutic composition useful for topical application to teeth and which includes a water-soluble, fluoride composition, an acid phosphate composition and a gelling agent.

Examples of different types of dispensing apparatus are shown, for example, in U.S. Pat. No. 4,175,326, which issued on Nov. 27, 1979 to J. M. Goodson and which teaches a hollow fiber device for delivery of therapeutic agents; U.S. Pat. No. 4,276,880, which issued on July 7, 1981 to O. Malmin, and which teaches a cannula for attachment to a dental instrument; U.S. Pat. No. 3,141,583, which issued on July 21, 1964 to W. S. Mapel et al., and which teaches a dispensing device for extrusion injection of viscous composition for veterinary purposes; U.S. Pat. No. 3,790,048, which issued to R. A. Luciano on Feb. 5, 1974, and which teaches an incremental dose dispenser; U.S. Pat. No. 3,504,673, which issued on Apr. 7, 1970 to F. Parisi, and which teaches an injection device with a dosage selector; and U.S. Pat. No. 1,586,302 which issued on May 25, 1926 to L. L. Funk, which teaches a flexible tooth cleaner and medicine carrier.

Recent studies with vitamins and, in particular, vitamin C (ascorbic acid) and vitamin B6 (pyridoxine) have suggested their anti-bacterial effectiveness. Such vitamin compositions have not, heretofore, been used in oral compositions.

Against the foregoing background, it is an object of the present invention to provide a composition for the preventive treatment of dental disease, said composition including one or more active bacterial growth inhibiting ingredients.

It is another object of the present invention to provide such a composition which further includes a gelling agent to permit the resultant composition to be delivered and retained below the gum line for effective preventative treatment of dental disease.

It is still another object of the present invention to provide a method for delivering such composition below the gum line for effective preventative treatment of dental disease.

SUMMARY OF THE INVENTION

The subject invention, in brief summary, comprises an oral composition for the preventative treatment of dental disease. The composition includes an active ingredient selected from the group consisting of ascorbic acid, pyridoxine hydrochloride, and an anti-inflammatory agent admixed in a vehicle including a gelling agent. Sodium fluoride may also be included. Method and apparatus for dispensing this composition are further provided.

BRIEF DESCRIPTION OF THE DRAWINGS

Certain specific embodiments of the invention have been chosen for purposes of illustration and description and are shown in the accompanying drawings forming a part of the specification, wherein:

FIG. 1 is a cutaway view of a side elevational view of the dispensing apparatus of the subject invention; and FIG. 2 is a partial perspective view of the apparatus.

DETAILED DESCRIPTION OF THE PREFERRED EMBODIMENT

The subject oral composition includes at least one active ingredient effective against periodontal microoranisms and a vehicle, preferably in the form of a gelling agent, which holds together the at least one active ingredient and which permits delivery of the active ingredient to the site of the potential disease activity, typically, to the space between the patient's teeth and gums.

The particular active ingredient or combination of active ingredients used in the subject composition must be capable of effectively combating the wide variety of subgingival periodontal bacteria which are present in a patient's mouth. Thus, in many instances, it is preferred to use a combination of different active ingredients to insure that the different types of microorganisms are effectively treated.

One active ingredient which should be included in the oral composition is ascorbic acid, i.e., vitamin C. Ascorbic acid serves the dual purpose of increasing host tissue resistance as well as in inhibiting bacterial growth. Ascorbic acid may be included in an effective amount, preferably between about 5% and about 30% by weight based on the weight of the total composition. In a preferred embodiment ascorbic acid is included in an amount between about 5% and about 15% by weight.

A second active ingredient which may be included in the composition is pyridoxine hydrochloride (i.e., vitamin B6). Pyridoxine hydrochloride has certain beneficial effects in healing as well as certain antibacterial properties. Pyridoxine hydrochloride may be added in an effective amount up to about 3.0% by weight based on the weight of the entire composition and preferably, in an amount of about 0.1% by weight.

A third active ingredient which may be included is an anti-inflammatory agent in order to effect the host response. Two preferred types of anti-inflammatory agents which may be used include acetyl salicylic acid (aspirin) and acetamidophenol (Tylenol). The anti-inflammatory agents may be included in an effective amount, preferably in an amount up to about 5.0% and preferably between about 0.35% and about 3.0% and most preferably about 1.5% by weight based on the weight of the entire composition.

A source of fluoride ions, preferably sodium fluoride, is still another active ingredient which may be included in the composition due to its particularly effective ability as an anti-bacterial agent. When preparing compositions for use in treating patients with severe cases of periodontal disease, inclusion of a source of fluoride ions is particularly important. Other sources of fluoride ions which may be used include, for example, other alkali metal fluorides, hydrofluoric acid, sodium bifluoride, potassium bifluoride, ammonium bifluoride, sodium silicofluoride, and stannous fluoride. When sodium fluoride is included, it may be included in concentrations up to about 40% by weight based on the weight of the entire composition.

Preferably, when a source of fluoride ions such as sodium fluoride is included, it is included, depending upon the patient to be treated, in either low concentrations of between about 0.05% and about 0.25% by weight or in higher concentrations of between about 0.25% and about 2.0% by weight, both calculated based on the weight of the entire composition.

The source of fluoride ions serves the dual purpose of inhibiting bacterial growth and decreasing the sensitivity of the roots of periodontally diseased teeth.

In a preferred embodiment, particularly effective in treating patients with advanced periodontal disease, calcium chloride in an amount up to about 5.0% by weight and preferably in an amount of about 1.0% by weight may be added. The calcium functions to complex with the fluoride which decreases the absorption of the fluoride. Additionally, the calcium fluoride complex provides a slow release of fluoride in the subgingival region. Orthophosphoric acid, preferably in an amount up to about 5.0% by weight and most preferably about 1.0% may also be added.

A preservative such as, for example sodium benzoate, a generally mild antiseptic and antipyretic, may be included in an amount up to about 3.0% by weight based on the weight of the entire composition and, preferably, in an amount between about 0.1 and about 0.25% and, most preferably, about 0.125% by weight. Additionally, a humectant such as, for example, glycerol may be 3.0% by weight, and preferably in an amount of about 10% by weight, based on the weight of the entire composition.

The vehicle in which the active ingredient or combination of active ingredients are carried should include one or more gelling agents in order to permit the resultant composition including its active ingredients to be localized at the particular site of the disease activity and to remain there for a period of time sufficient to allow the active ingredients to attack the periodontal subgingival microflora. Gelling agents selected from the group consisting of gum tragacanth, gum arabic, agar-agar, hydroxyethyl cellulose, and carboxylmethyl cellulose, have proven particularly effective in providing an adhesive gel wherein the active ingredients are retained at the site of disease activity for at least twenty-four (24) hours after application. A combination of the following gelling agents is preferred: gum tragacanth, gum arabic and agar-agar and, preferably, in a total amount between about 1.0% and 20% and most preferably between about 4% and 5% by weight.

The gelling agents may be admixed with distilled water in an amount sufficient to yield 100% and, preferably, water comprises between about 30% and about 90% the composition. Other additives and stabilizers such as, for example, citric acid, may be included in appropriate amounts as well as agents for taste, flavor, color, fragrance and the like.

In order to prepare the subject composition, the active ingredients are admixed with preheated distilled water followed by the addition of the gelling agents.

The specific formulations will vary depending upon the condition of the patients to be treated. For example, in patients with little or no disease or inflammation and no bone loss or gingivitis, it is usually not necessary to include fluoride as an active ingredient. The following formulation has proven effective in treating such patients:

| Component | Range | Preferred Amount |
|---|---|---|
| sodium benzoate | 0–0.25% | 0.125% |
| ascorbic acid | 5–30% | 10% |

-continued

| Component | Range | Preferred Amount |
| --- | --- | --- |
| anti-inflammatory agent | 0.35%–3% | 1.5% |
| pyridoxine hydrochloride | 0–0.2% | 0.1% |
| glycerol | 5–30% | 10.0% |
| gum tragacanth | 1.0–9.0% | 3.5% |
| gum arabic | 0–0.5% | 0.5% |
| agar-agar | 0.5%–1.0% | 0.5% |
| water | balance | balance |

In contrast, the following formulation is preferred for patients having incipient or moderate disease as evidence by incipient alveolar bone loss and minimal periodontal pocketing:

| Component | Range | Preferred Amount |
| --- | --- | --- |
| sodium fluoride | 0.05%–0.25% | 0.25% |
| sodium benzoate | 0–0.25% | 0.125% |
| ascorbic acid | 5–30% | 10.0% |
| anti-inflammatory agent | 0–3.0% | 1.5% |
| pyridoxine hydrochloride | 0–0.2% | 0.1% |
| glycerol | 5.0–20.0% | 10.0% |
| citric acid | 0–1.0% | 0.1% |
| gum tragacanth | 1.0–9.0% | 3.5% |
| gum arabic | 0–0.5% | 0.5% |
| agar-agar | 0.5%–10% | 0.5% |
| water | balance | balance |

The following formulation is preferred for patients having advance periodontal disease as evidence by significant alveolar bone loss and periodontal pocketing:

| Component | Range | Preferred Amount |
| --- | --- | --- |
| sodium fluoride | 0.25–4.0% | 1.0% |
| calcium chloride | 0–4.0% | 1.0% |
| orthophosphoric acid | 0–3.5% | 1.0% |
| sodium benzoate | 0–0.25% | 0.125% |
| ascorbic acid | 5.0–30.0% | 10.0% |
| anti-inflammatory agent | 0–1.5% | 1.5% |
| pyridoxine hydrochloride | 0–0.2% | 0.1% |
| glycerol | 5–20% | 10% |
| gum tragacanth | 1.0–9.0% | 3.5% |
| gum arabic | 0–0.5% | 0.5% |
| agar-agar | 0.5%–1.0% | 0.5% |
| water | balance | balance |

The composition of the subject invention may be applied or otherwise delivered to the site of periodontal disease by a number of different applicators such as, for example, cannulas, injection, gums and other dispensers. A preferred dispensing apparatus is shown in FIGS. 1 and 2 wherein the dispensing apparatus, referred to generally by reference numeral 10, is hand-held, finger-actuated and motorized. Dispensing apparatus 10, which is composed of a head 20 and a base or handle 30, both of which are substantially hollow, are preferably fabricated from molded thermoplastic material or from metal.

Head 20 includes upper and lower sections 21 and 22, respectively, which are hinged along one edge to permit access to the interior portion thereof. The anterior portion of head 20 is hollow to permit insertion of a gel-containing cartridge 23 adapted to deliver the gel composition to the treatment site of a patient through a stainless steel needle 24 contained within a tip 25 at the anterior end of head 20. Gel cartridge 23 is hollow at both ends and the gel composition may be introduced therein through either end prior to insertion of the cartridge 23 into head 20. Once inserted into the head, needle 24 is adapted to extend into one end of gel cartridge 23 and a solid rubber gasket 26 is provided at the distal end of the tip 25 to ensure a tight fit between the cartridge 23 and the tip 25.

The shape, angle and dimension of the tip 25 are particularly important in insuring that the apparatus delivers the composition directly to the spaces between the teeth and gums of a patient. Unlike a hypodermic needle, the orifice 25A of tip 25 is gently rounded so as to ensure safe and comfortable use. A number of different interchangeable tips may be utilized for use with the subject dispensing device. The internal diameter of needle 24 is generally about 3 mm at its distal end. In one embodiment, particularly suitable for use with patients with advanced disease dispensing of greater amounts of the composition is required, the internal diameter of the needle 24 remains generally constant but may decrease to 0.4 mm at its anterior dispensing end. In an alternative embodiment for use with patients with moderate disease, the length of the tip 25 is reduced by about 2 mm and the internal diameter of the needle 24 tapers to between about 0.2 mm and 0.5 mm at its anterior end.

A plunger 27 is provided within the posterior end of head 20 and is retained in place within a cut-out section therein. Plunger 27, which is preferably fabricated from hard plastic, includes a elongated shaft 27A having a rubber nipple 28 at its anterior end adapted to be inserted into the open end of gel cartridge 23. Nipple 28 is so dimensioned as to precisely fit the inner walls of cartridge 23. Plunger shaft 27A includes a plurality of teeth 29 along its lower surface adapted to engage gears 31 contained within the base 30. An upturned gripping portion 27B is provided on the upper surface of the shaft 27A for permitting easy retraction of the plunger 27 after use. Upon engagement of the gears 31 and teeth 29, the rubber nipple 28 of plunger 27 is driven into gel cartridge 23 through its posterior open end forcing the gel composition out of the cartridge 23 through needle 24 in tip 25 for dispensing.

Base 30 is interconnected to the head 20 and forms about a 120° angle with the head 20. Contained within base 30 are a plurality of gears 31 adapted to engage teeth 29 on the lower surface of plunger 27 for driving the plunger 27 causing the rubber nipple 28 at the end of the plunger 27 to enter gel cartridge 23 and force the composition out through needle 24. Base 30 includes an electric motor 32 adapted to cause the gears 31 to turn and one or more batteries 33 for powering said motor 32. An external button or switch 34 is provided for actuating the motor 32. A cap 35 is provided at the distal end of base 30 threadably connected thereto to permit access to the batteries.

Both the cartridge 23 and the tip 25 may be conveniently removed for replacement by merely opening the upper section 21 of head 20. Both the tip 25 and the needle 24 may be prepackaged to insure sterility. At the completion of a treatment, upper section 21 of head 20 is simply opened, plunger 27 retracted from the cartridge 23 and the cartridge 23 and tip 25 is discarded. For renewed operation, a fresh composition-containing cartridge 23 and sterile tip 25 are inserted into the head 20 and the upper section 21 is closed. The patient himself or a professional would then position the tip 25 of the apparatus 10 adjacent the treatment site, actuate the motor 32 by depression of switch 34 causing plunger 27 to force the composition gel from cartridge 23 to pass through needle 24 in tip 25 and be dispensed to the site to be treated.

The further examples serve to further illustrate the present invention and are not to be construed as limiting the scope thereof.

EXAMPLE I

In order to evaluate the effectiveness of one of the compositions of the subject invention, the following test was performed. A standard innoculum of 100 microliters from an overnight growth of *Actinomyces viscosus* T 14 V was innoculated into each of several tubes containing 5 milliliters of an enriched nutrient broth such as trypticase soy broth of brain heart infusion. Thereafer, 10 to 100 microliters of the following composition was introduced into the broth:

| Component | Weight % |
| --- | --- |
| Sodium Benzoate | 0.125% |
| Ascorbic Acid | 10% |
| Acetylsalicylic Acid | 1.5% |
| or Acetamidophenol | 1.5% |
| Pyridoxine Hydrochloride | 0.10% |
| Glycerol | 10.0% |
| Gum Tragacanth | 3.5% |
| Gum Arabic | 0.5% |
| Agar-Agar | 0.5% |
| Water | balance |

Two additional compositions were also prepared, one containing only ascorbic acid and the other only pridoxine hydrochloride as active ingredients in a 10 mg and a 50 mg concentration, respectively.

The mixture of the bacterial innoculum and the three compositions plus bacteria and controls containing gel, glycerol and broth, and broth alone, were then incubated anaerobically for 16-18 hours at 37° C. The tubes were removed and analyzed for optical density for 550 n.m. using a spectrophotometer. The optical density was recorded against a blank containing the uninnoculated broth and the lowest concentration of the composition approaching the reading achieved by the blank was considered the minimal inhibitory concentration. The compositions including only the ascorbic acid and the pyridoxine hydrochloride served to inhibit bacterial growth, but the composition which included all active ingredients, demonstrated substantial inhibition of growth.

The results were confirmed in an agar plate experiment. A standard innoculum of *A. viscosus* T 14 V was streaked on an agar plate containing trypticase soy agar supplemented with 5% sheep's defibrinated blood. To this plate a series of drops of different compositions were added as follows: one series of drops containing the vehicle alone without any active ingredient; one series containing each active ingredient separately; and one series containing the combination of all active ingredients. All plates were incubated anaerobically at 37° C. for 24 hours. The plates were removed and a standard microbiological loop was used to pierce the center of the drop. The loop was then streaked onto a second, uninnoculated agar plate, incubated, removed, and the ability of the concentration to cause inhibition of growth was determined by the analysis of the number of organisms seen on the second plate. Once again, the combination of active ingredients proved to be more effective than the individual components.

EXAMPLE II

In order to evaluate the effectiveness of another version of the composition of the subject invention, a series of bacteria adherence tests were performed.

A series of enamel squares were prepared from extracted teeth and were fastened to a holder and the holder to the cap of an autoanalyzer tube. The sides of the enamel and its back were blocked out with wax. A 100 microliter innoculum of *A. viscosus* was placed in 300 microliters of trypticase soy broth contained in the autoanalyzer tube and a drop of the composition to be tested was placed on the exposed surface of enamel. The compositions listed were as follows: (1) vehicle alone; (2) vehicle and sodium fluoride; (3) vehicle and the following active ingredient: sodium benzoate, ascorbic acid and pyridoxine hydrochloride; and (4) a composition including the following components:

| Component | Weight % |
| --- | --- |
| Sodium Fluoride | 0.250% |
| Sodium Benzoate | 0.125% |
| Ascorbic Acid | 10.0% |
| Acetylsalicylic Acid | 1.5% |
| Pyridoxine Hydrochloride | 0.100% |
| Glycerol | 10.0% |
| Citric Acid | 0.1% |
| Gum Tragacanth | 3.5% |
| Gum Arabic | 0.5% |
| Agar-Agar | 0.5% |

The gel treated enamel squares were then placed in the innoculum and incubated anerobically for 24-28 hours, removed, and tested for the pH on the surface of the square. The pH was determined by a microelectrode placed directly on the surface of the enamel square. The results indicated as follows: the vehicle alone did not alter the pH and thus readings of 5.4-5.5 were found; the vehicle with the fluoride (composition no. 2) elevated the pH to approximately 6.70 while the composition no. 4 elevated the pH to approximately 6.40.

The effectiveness of composition no. 4 in inhibiting bacterial adherence to tooth surfaces was further revealed by the following experiment. Enamel squares were prepared as described, set in wax, and placed in the bottom of 4 ml. Wheatone tubes. The tubes were innoculated with 100 microliters of an innoculum of *A. viscosus* and 2 ml. of trypticase soy broth. The squares were treated with one drop of various types of the compositions described above. The treated enamel square plus the innoculum were incubated anerobically for 24-28 hours. On removal, it was noticed that the drop in all cases remained visible for up to 24-36 hours following drop placement on the enamel surface indicating the adhesiveness and resilience of the composition. Squares were removed from their wax supports and placed in 2 mls. Of sterile broth as a wash, to remove non-adherent bacteria. They were then transferred to 4 milliliters of sterile broth so that they may be treated by ultrasonic vibration to remove enamel adherent bacteria. One hundred microliters and ten microliters of the sonically treated bacteria were streaked on a blood agar plate, which were incubated aneorbically for 24-48 hours at 37° C. Colonies were then counted. Composition no. 4 demonstrated complete inhibition of adherence in this test, while composition no. 2 (the vehicle and the sodium fluoride) was the least inhibitory. The vehicle alone (composition no. 1) showed no inhibitory effect. Similar results were found when the sonically treated cells were stained with acridine orange and counted under a fluorescent microscope at 1000 times magnification.

EXAMPLE III

A preliminary evaluation of the in vivo effectiveness of the preferred formulation given in Example II was conducted on three patients having advanced periodontal disease. In each of these patients, two periodontal pockets with similar depth and bone loss were chosen. An endodontic absorbent point was used to sample each pocket to determine the ratio of motile forms to non-motiles as observed by dark-field microscopy at 1000 times magnification. Disease activity, as measured by motile organisms, correlates well with bleeding (Armitage et al. 1982) and, thus, a bleeding index as modified from Mazza et al. (1981) was used as a second clinical parameter. At the outset the two pockets were similar with respect to the number of motile organisms and the bleeding index.

Into one pocket the vehicle (composition no. 1) alone was delivered, while into the second pocket, composition no. 4 was delivered. Seven days later, the patient was recalled and retested with respect to the percentage of motile v. non-motile organisms and the change in the bleeding index. The percentage of motile organisms was reduced by 16.4% in the pocket treated with the preferred formulation as compared to the vehicle control pocket. In addition, the bleeding index was reduced from a starting point of 4.3 to 1.7 as compared to a 4.3 to 4.0 reduction in the vehicle control pocket.

In a second series of experiments, pockets were cleaned out first and, then, compositions no. 1 and no. 4 were applied once for one week. A 25.3% decrease in the number of motile organisms as compared to the vehicle control were seen when observations of the microbial re-population of the cleaned out pocket area was made. While the bleeding index was lower in the pockets receiving the preferred formulation, the differences were not that outstanding as a result of the cleaning procedure. Two patients reported tasting the agents for two days following placement. In addition, it is certain that use of the compositions for more than one time during the week would give better results.

While the foregoing examples serve to illustrate the preparation and use of certain specific formulations of the composition of the subject invention, it will be appreciated that similar compositions can also be effectively used. Accordingly, the subject invention should only be limited by the scope of the appended claims.

Wherefore I claim:

1. An oral composition for the preventative treatment of dental disease, said composition including:
    ascorbic acid in an amount between about 5% and about 30% by weight and pyridoxine hydrochloride in an amount up to about 3% by weight as active ingredients, both calculated based on the weight of the total composition;
    a gelling agent in an amount between about 1% and about 20% by weight based on the weight of the total composition; and a vehicle.

2. The composition of claim 1 wherein said active ingredients further include a source of fluoride ions in an amount between about 0.01% and about 5.0% by weight based on the weight of the total composition.

3. The composition of claim 1 wherein said active ingredients further include at least one anti-inflammatory agent selected from the group consisting of acetylsalicylic acid and acetamidophenol in an amount up to about 5% by weight based on the weight of the total composition.

4. The composition of claim 1 wherein said vehicle includes water.

5. The composition of claim 1 wherein said composition includes at least one gelling agent selected from the group consisting of gum tragacanth, gum arabic, agar-agar, hydroxyethyl cellulose and carboxylmethyl cellulose in an amount between about 1.0% and about 20% by weight based on the weight of the total composition.

6. The composition of claim 1 wherein said composition further includes citric acid in an amount up to about 1% by weight based on the weight of the total composition.

7. The composition of claim 1 wherein said composition further includes calcium chloride in an amount up to about 4.0% by weight and orthophosphoric acid in an amount up to about 3.5% by weight, both based on the weight of the total composition.

8. The composition of claim 1 further including additives selected from the group consisting of preservatives, humectants, and taste and flavoring agents.

9. The oral composition of claim 1 further including sodium fluoride as an active ingredient.

10. An oral composition for the preventative treatment of dental disease, said composition including:
    ascorbic acid in an amount between about 5% and about 30% by weight and pyridoxine hydrochloride in an amount up to about 3% by weight as active ingredients, both calculated based on the weight of the total composition;
    at least one anti-inflammatory agent selected from the group consisting of acetylsalicylic acid and acetamidophenol in an amount up to about 5% by weight based on the weight of the total composition;
    a source of fluoride ions in an amount between about 0.01% and about 5% by weight based on the weight of the total composition; and
    a vehicle which includes a gelling agent.

11. A method for the preventative treatment of dental disease, said method comprising the steps of:
    providing a composition including:
        ascorbic acid in an amount between about 5% and about 30% by weight and pyridoxine hydrochloride in an amount up to about 3% by weight as active ingredients, both calculated based on the weight of the total composition;
        a gelling agent in an amount between about 1% and about 20% by weight based on the weight of the total composition; and
        a vehicle; and
    dispensing said composition directly to a treatment site between a subject's gum and teeth.

12. The method of claim 11 wherein said composition includes a source of fluoride ions in an amount between about 0.05% and about 2.0% and at least one anti-inflammatory agent selected from the group consisting of acetylsalicylic acid and acetamidophenol in an amount up to about 3% by weight based on the weight of the total composition.

13. The method of claim 11 wherein said gelling agent is selected from the group consisting of gum tragacanth, gum arabic, agar-agar, hydroxethyl cellulose and carboxylmethyl cellulose in an amount between about 1.5% and about 10% by weight based on the weight of the total composition.

14. The method of claim 11 wherein said composition is dispensed by an oral applicator which includes a disposable tip adapted to fit between a subject's gum and teeth.

* * * * *